United States Patent
Lee et al.

(10) Patent No.: US 9,131,918 B2
(45) Date of Patent: Sep. 15, 2015

(54) 3-DIMENSIONAL ULTRASOUND IMAGE PROVISION USING VOLUME SLICES IN AN ULTRASOUND SYSTEM

(75) Inventors: Suk Jin Lee, Seoul (KR); Jung Kim, Seoul (KR)

(73) Assignee: SAMSUNG MEDISON CO., LTD., Hongcheon-Gun, Gangwon-Don (KR)

( * ) Notice: Subject to any disclaimer, the term of this patent is extended or adjusted under 35 U.S.C. 154(b) by 256 days.

(21) Appl. No.: 12/727,019

(22) Filed: Mar. 18, 2010

(65) Prior Publication Data

US 2010/0256492 A1    Oct. 7, 2010

(30) Foreign Application Priority Data

Apr. 1, 2009  (KR) .................. 10-2009-0028281

(51) Int. Cl.
*A61B 8/00* (2006.01)
*A61B 8/08* (2006.01)
*G01S 7/52* (2006.01)
*G01S 15/89* (2006.01)

(52) U.S. Cl.
CPC . *A61B 8/00* (2013.01); *A61B 8/463* (2013.01); *A61B 8/483* (2013.01); *G01S 7/52073* (2013.01); *G01S 7/52074* (2013.01); *G01S 15/8993* (2013.01)

(58) Field of Classification Search
CPC ...... A61B 8/483; A61B 8/463; A61B 8/5238; A61B 8/00; A61B 6/463
USPC ......................................... 600/407, 437–475
See application file for complete search history.

(56) References Cited

U.S. PATENT DOCUMENTS

| | | | |
|---|---|---|---|
| 6,537,219 B2* | 3/2003 | Poland et al. ................ | 600/447 |
| 7,507,204 B2 | 3/2009 | Shim et al. | |
| 2005/0240104 A1 | 10/2005 | Shim et al. | |
| 2007/0100238 A1* | 5/2007 | Kwon et al. ................ | 600/437 |
| 2007/0255136 A1 | 11/2007 | Kristofferson et al. | |
| 2007/0255139 A1 | 11/2007 | Deschinger et al. | |

(Continued)

FOREIGN PATENT DOCUMENTS

| EP | 1775601 A1 | 10/2006 |
|---|---|---|
| EP | 1 775 601 A1 | 4/2007 |

(Continued)

OTHER PUBLICATIONS

European Search Report for Application No. 10154490.6-2319, mailed May 27, 2010, 8 pages.

(Continued)

*Primary Examiner* — Mark Remaly
(74) *Attorney, Agent, or Firm* — McDermott Will & Emery LLP

(57) ABSTRACT

Embodiments for providing a plurality of 3-dimensional ultrasound images by using a plurality of volume slices in an ultrasound system are disclosed. The ultrasound system comprises: an ultrasound data acquisition unit configured to transmit and receive ultrasound signals to and from a target object to acquire ultrasound data; a volume data forming unit configured to form volume data by using the ultrasound data; a user input unit for allowing a user to input a user instruction; and a processing unit configured to set a plurality of volume slice regions having different widths in the volume data in response to the user instruction and form a plurality of 3-dimensional ultrasound images by using volume slices defined by the volume slice regions.

26 Claims, 7 Drawing Sheets

(56) References Cited

U.S. PATENT DOCUMENTS

| | | | |
|---|---|---|---|
| 2008/0051653 A1 | 2/2008 | Choi et al. | |
| 2009/0227869 A1 | 9/2009 | Choi | |

FOREIGN PATENT DOCUMENTS

| | | | |
|---|---|---|---|
| JP | 2005-218520 A | 8/2005 | |
| JP | 2007-082649 A | 4/2007 | |
| JP | 2007-111532 A | 5/2007 | |

OTHER PUBLICATIONS

Merz, Current 3D/4D ultrasound technology in prenatal diagnosis, Eur. Clinics Obstet. Gynaccol., vol. 1, pp. 184-193.

Korean Office Action issued in Korean Patent Application No. KR 10-2009-0028281 filed Apr. 20, 2011.

Japanese Office Action issued in Application No. 2010-061367 dated Feb. 12, 2014.

Non-final Office Action dated Aug. 26, 2014 issued in Japanese Patent Application No. 2010-061367 (English translation).

* cited by examiner

FIG. 7

| | | |
|---|---|---|
| $DR_1$ | $DR_2$ | $DR_3$ |
| $DR_4$ | $DR_5$ | $DR_6$ |
| $DR_7$ | $DR_8$ | $DR_9$ |

3-DIMENSIONAL ULTRASOUND IMAGE PROVISION USING VOLUME SLICES IN AN ULTRASOUND SYSTEM

CROSS-REFERENCE TO RELATED APPLICATIONS

The present application claims priority from Korean Patent Application No. 10-2009-0028281 filed on Apr. 1, 2009, the entire subject matter of which is incorporated herein by reference.

TECHNICAL FIELD

The present disclosure generally relates to ultrasound systems, and more particularly to an ultrasound system and method of providing a plurality of 3-dimensional ultrasound images using volume slices.

BACKGROUND

An ultrasound system has become an important and popular diagnostic tool since it has a wide range of applications. Specifically, due to its non-invasive and non-destructive nature, the ultrasound diagnostic system has been extensively used in the medical profession. Modern high-performance ultrasound diagnostic systems and techniques are commonly used to produce two or three-dimensional diagnostic images of internal features of an object (e.g., human organs).

Generally, the ultrasound system transmits ultrasound signals into a target object and receives echo signals reflected from the target object. The ultrasound system may form volume data consisting of a plurality of frames based on the received echo signals. Conventionally, the conventional ultrasound system sets one region of interest (ROI) on a plane image and forms a 3-dimensional ultrasound image corresponding to the ROI. Thus, when the undesirable 3-dimensional ultrasound image is formed, a user should reset the ROI.

SUMMARY

Embodiments of providing a plurality of 3-dimensional ultrasound images by using volume slices are disclosed herein. In one embodiment, by way of non-limiting example, an ultrasound system may include: an ultrasound data acquisition unit configured to transmit and receive ultrasound signals to and from a target object to acquire ultrasound data; a volume data forming unit configured to form volume data by using the ultrasound data; an user input unit for allowing a user to input a user instruction; and a processing unit configured to set a plurality of volume slice regions having different widths in the volume data in response to the user instruction and form a plurality of 3-dimensional ultrasound images by using volume slices defined by the volume slice regions.

In one embodiment, a method of providing a plurality of 3-dimensional ultrasound images, comprises: a) transmitting and receiving ultrasound signals to and from a target object to acquire ultrasound data; b) forming volume data comprising a plurality of sectional planes by using the ultrasound data; c) receiving a user instruction from a user; and d) setting a plurality of volume slice regions having different widths in the volume data in response to the user instruction and forming a plurality of 3-dimensional ultrasound images by using volume slices defined by the volume slice regions.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 7 is a schematic diagram showing an example of a layout having a plurality of display regions.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
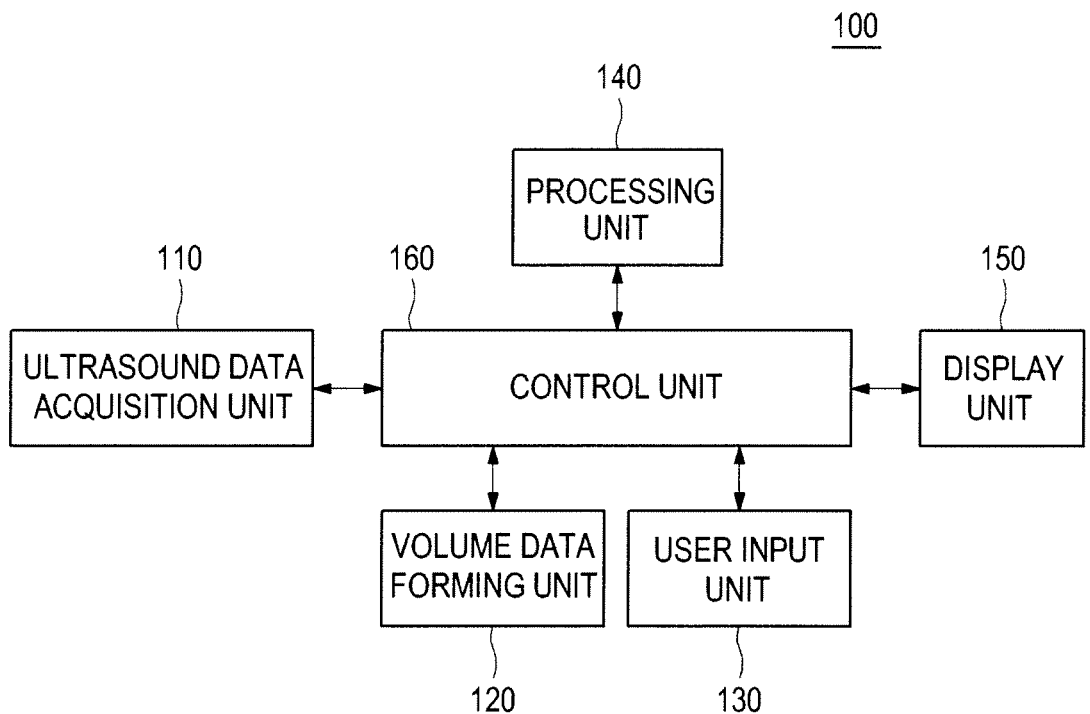
FIG. 1 is a block diagram showing an illustrative embodiment of an ultrasound system.

FIG. 1 is a block diagram showing an illustrative embodiment of an ultrasound system. The ultrasound system 100 may include an ultrasound data acquisition unit 110. The ultrasound data acquisition unit 110 may be configured to transmit ultrasound signals to a target object and receive echo signals reflected from the target object. The ultrasound data acquisition unit 110 may be further configured to form ultrasound data based on the echo signals.

Figure 2:
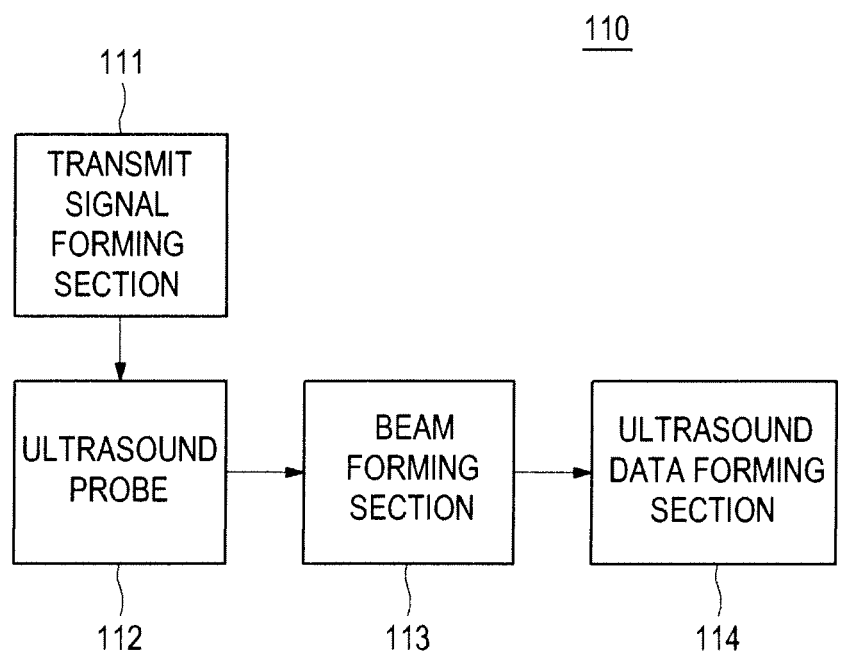
FIG. 2 is a block diagram showing an illustrative embodiment of an ultrasound data acquisition unit.

Referring to FIG. 2, the ultrasound data acquisition unit 110 may include a transmit (Tx) signal generating section 111. The Tx signal generating section 111 may be configured to generate Tx pulses and apply delays to the Tx pulses to form a Tx pattern thereof. The Tx pattern may be controlled according to an image mode such as a B-mode, an M-mode, a Doppler mode, etc.

The ultrasound data acquisition unit 110 may further include an ultrasound probe 112. The ultrasound probe 112 may contain a plurality of transducer elements 112 to receive the Tx pulses for conversion into ultrasound signals that may travel into the target object. The ultrasound probe 112 may receive ultrasound echo signals reflected from the target object and convert them into electrical receive signals, which may be analog signals. The ultrasound probe 112 may include a 3-dimensional probe, a 2-dimensional array probe or the like.

The ultrasound data acquisition unit 110 may further include a beam forming section 113. The beam forming section 113 may convert the electrical receive signals into digital signals and delay the digital signals in consideration of distances between the transducer elements and focal points. The beam forming section 113 may further sum the delay digital signals to form receive-focused signals.

The ultrasound data acquisition unit 110 may further include an ultrasound data forming section 114. The ultrasound data forming section 114 may be configured to form ultrasound data based on the receive-focused signals. The ultrasound data forming section 114 may be further configured to perform a variety of signal processing (e.g., gain adjustment, filtering, etc.) upon the receive-focused signals.

Referring back to FIG. 1, the ultrasound system 100 may further include a volume data forming unit 120. The volume data forming unit 120 may be configured to form volume data based on the ultrasound data. In one embodiment, the volume data may include a plurality of frames.

The ultrasound system 100 may further include a user input unit 130 allowing a user to input user instructions. In one embodiment, the user input unit 130 may include at least one of a control panel, a mouse, a keyboard and the like. The user instructions may include a first user instruction for setting a region of interest (ROI) on each of the plurality of frames and a second user instruction for selecting a reference plane from the volume data. The user instructions may further include a third user instruction for setting a plurality of volume slice regions to obtain volume slices having different depths (i.e., different widths) for forming a plurality of 3-dimensional ultrasound images based on the volume slices. That is, the plurality of volume slice regions represents a rendering range of different widths in the volume data. The user instruction may further include a fourth user instruction for setting a layout including a plurality of display regions to display the plurality of 3-dimensional ultrasound images. A detailed description of the reference plane, the volume slice regions, the volume slices and the layout will follow. The user instructions may further include a fifth user instruction for setting whether or not to indicate an image corresponding to the reference plane (hereinafter, referred to as a "reference plane image") and an orientation help (OH) view, and also include a sixth user instruction for setting intervals between the plurality of volume slice regions. The user instructions may further include a seventh user instruction for setting a reference volume slice among the plurality of volume slices.

The ultrasound system 100 may include a processing unit 140. The processing unit 140 may be configured to set a plurality of volume slice regions on the reference plane image in response to the third user instruction. The processing unit 140 may be further configured to slice the volume data perpendicular to the volume slice regions to obtain the plurality of volume slices. The processing unit 140 may form a plurality of 3-dimensional ultrasound images by using the volume slices. In one embodiment, a central processing unit or a graphic processing unit may be adopted as the processing unit 140.

Figure 3:
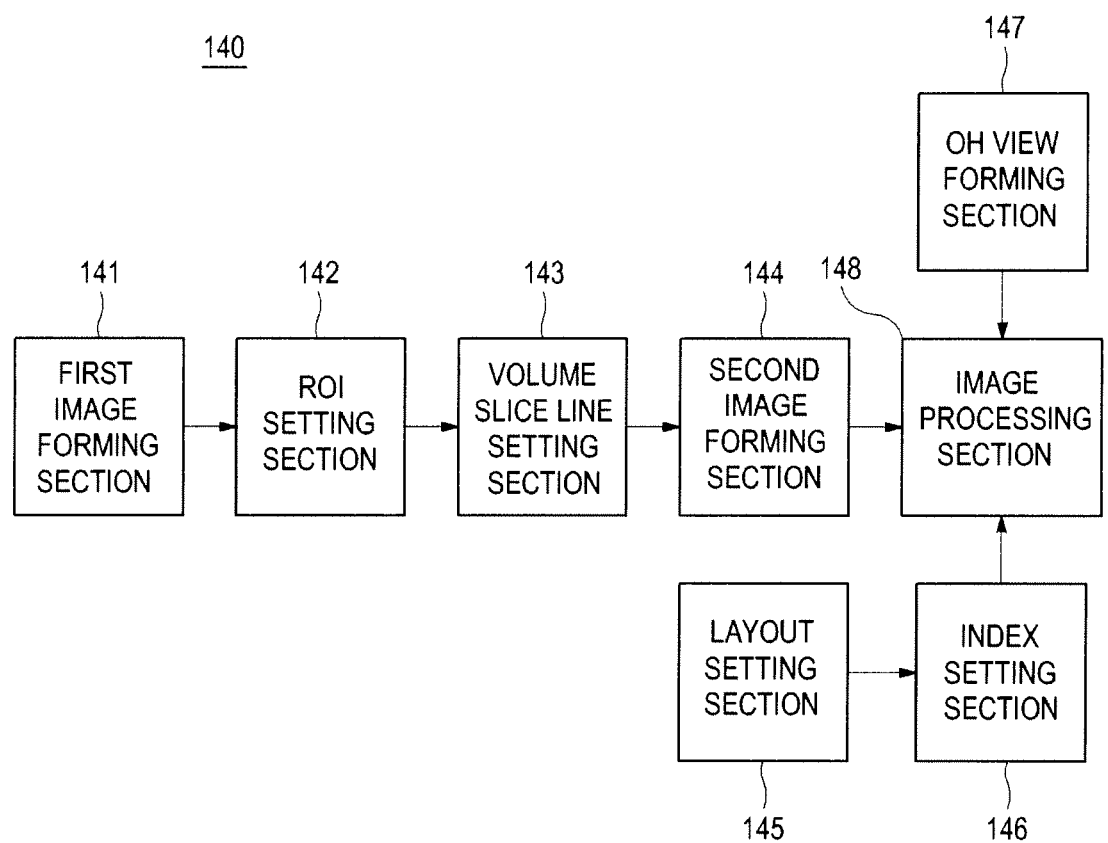
FIG. 3 is a block diagram showing an illustrative embodiment of a processing unit.
Figure 4:
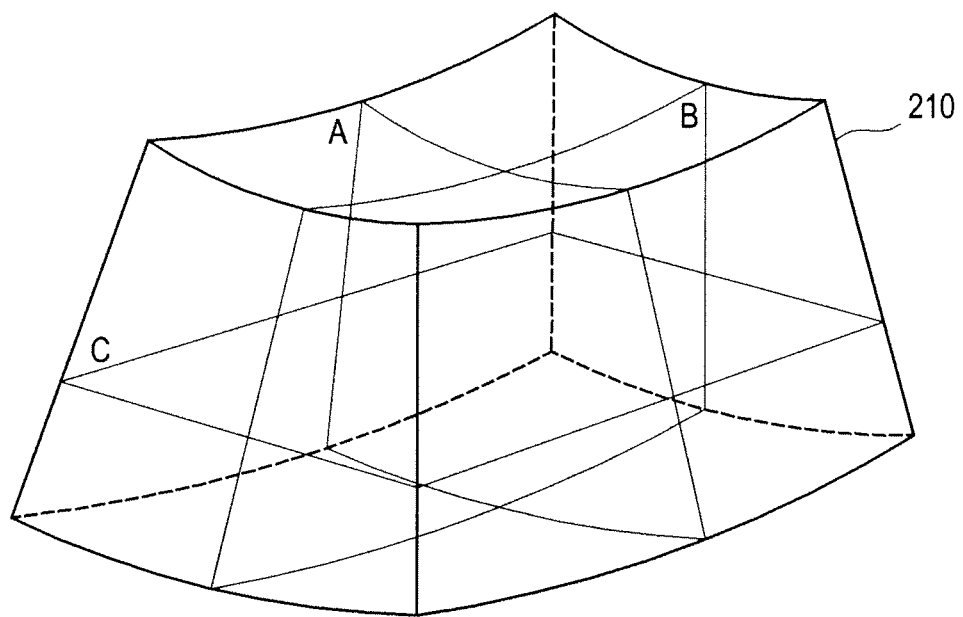
FIG. 4 is a schematic diagram showing an example of volume data.
Figure 5:
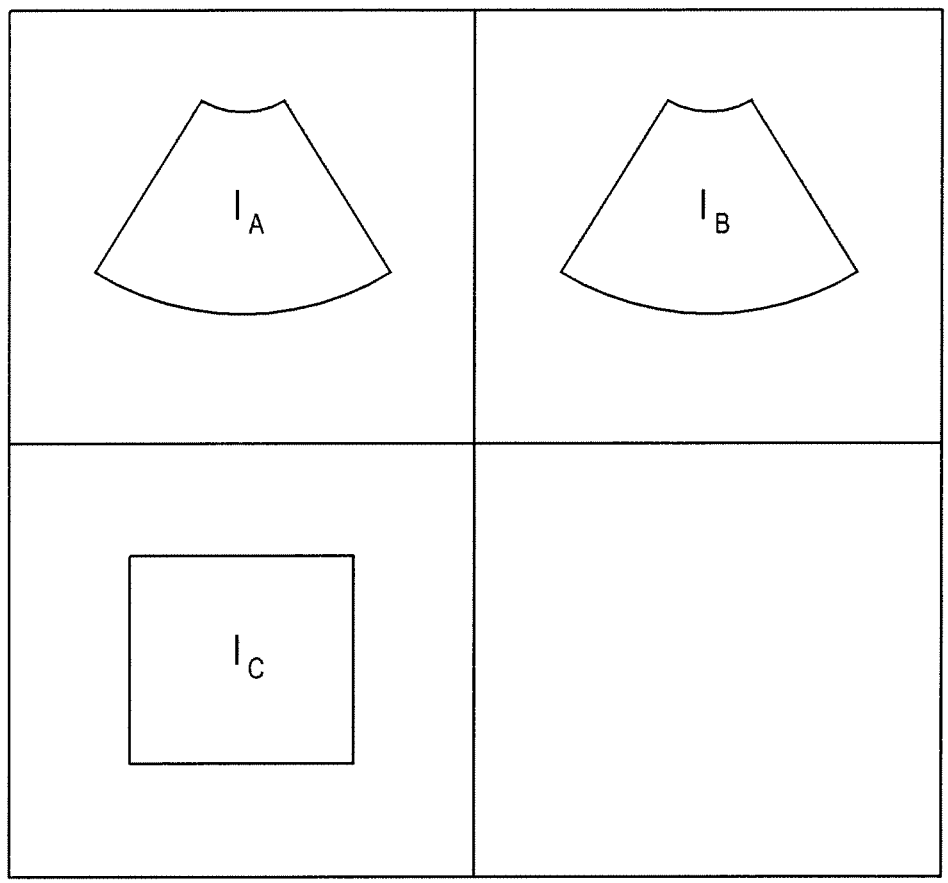
FIG. 5 is a schematic diagram showing examples of an A plane image, a B plane image and a C plane image.

FIG. 3 is a block diagram showing an illustrative embodiment of the processing unit 140. Referring to FIG. 3, the processing unit 140 may include a first image forming section 141. The first image forming section 141 may form a plurality of images corresponding to a plurality of planes, which are perpendicular to each other in the volume data (hereinafter, referred to as "plane images"). For example, as illustrated in FIG. 5, the first image forming section 141 may form frame images corresponding to an A plane, a B plane and a C plane set in the volume data 210, as show in FIG. 4. In one embodiment, the frame images corresponding to the A, B and C planes will be referred to as A, B and C plane images $I_A$, $I_B$ and $I_C$.

Figure 6:
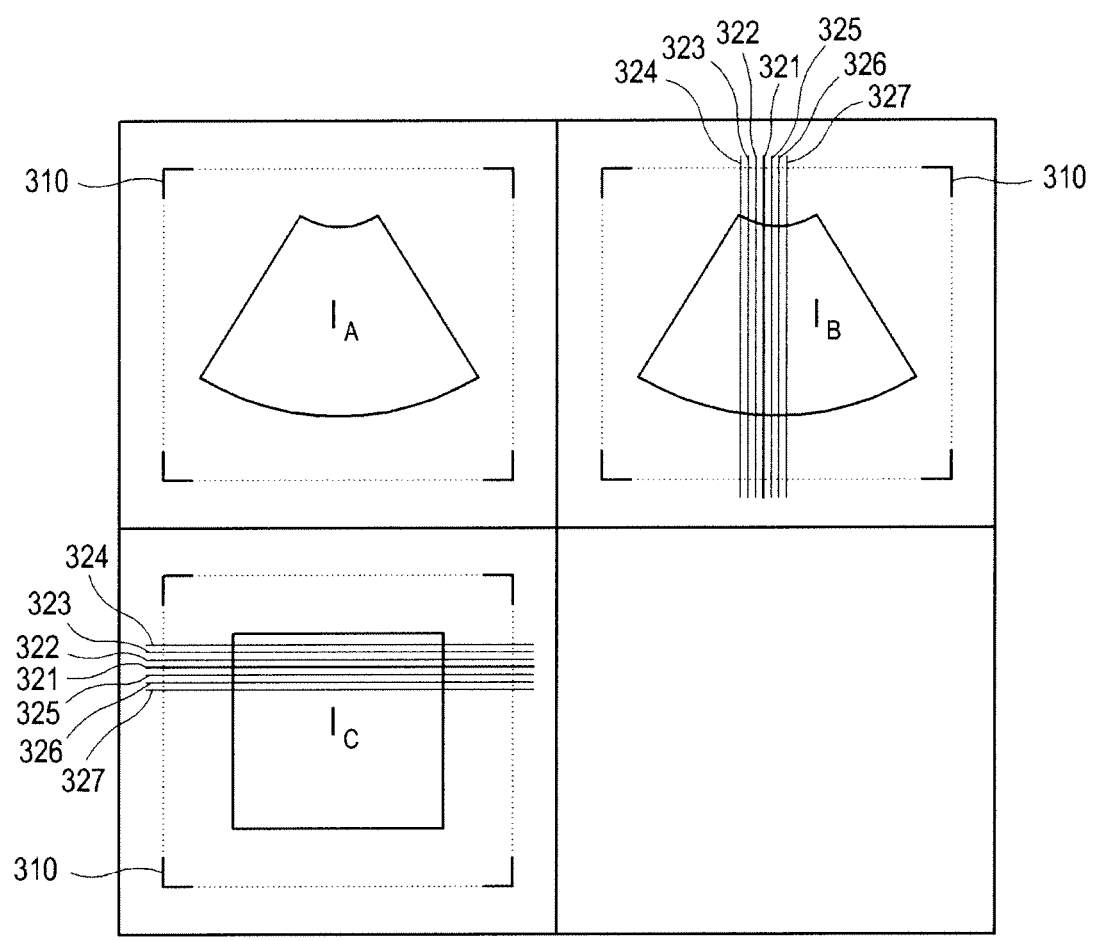
FIG. 6 is a schematic diagram showing an example of setting a region of interest on A-C plane images and a plurality of volume slice regions on B and C plane images.

The processing unit 140 may further include an ROI setting section 142. The ROI setting section 142 may be configured to set an ROI on each of the plane images in response to the first user instruction. For example, the ROI setting section 142 may set the ROI 310 on each of the A to C plane images $I_A$-$I_C$, as illustrated in FIG. 6.

The processing unit 140 may further include a volume slice region setting section 143. The volume slice region setting section 143 may set a reference plane among the plurality of A, B and C planes in response to the second user instruction. For example, the reference plane may be a B plane or C plane. The volume slice region setting section 143 may further set a plurality of volume slice regions on a reference plane image to determine rendering ranges of different volume depths for forming a plurality of 3-dimensional ultrasound images in response to the third user instruction. For example, the volume slice region setting section 143 may set first to seventh volume slice regions 321-327 on the reference plane image (B plane image or C plane image), as illustrated in FIG. 6. In one embodiment, the direction of the volume depth may represent an axial direction, a lateral direction or an elevation direction according to the selected reference plane.

Although the above embodiment has been described that the second to fourth volume slice regions 322-324 are set on the left of the first volume slice 321 and the fifth to seventh volume slice regions 325-327 are set on the right of the first volume slice 321, the setting of the volume slice regions 321-327 may not be limited thereto. The number and position of the volume slice regions may be arbitrarily set according to the third user instruction.

Figure 8:
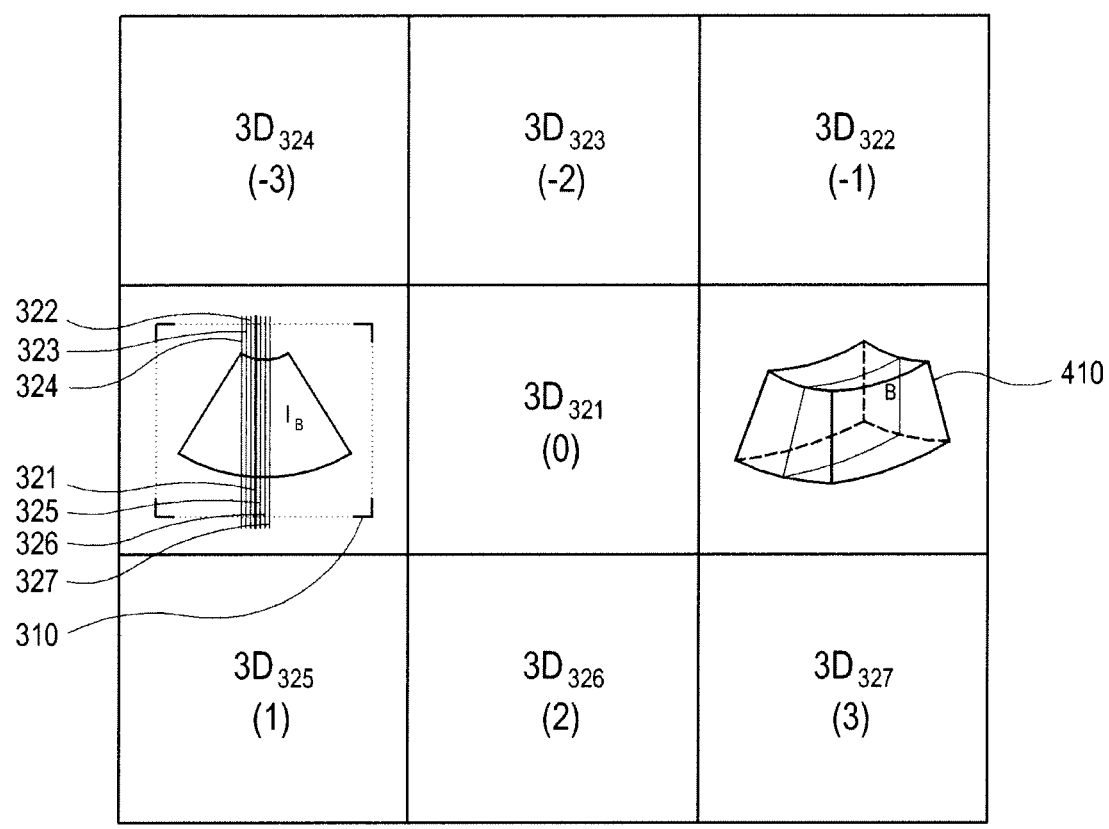
FIG. 8 is a schematic diagram showing an example of indicating a reference plane image, an OH view and indices on a layout.

Further, the volume slice region setting section 143 may further adjust intervals between the volume slice regions set on the reference plane image in response to the sixth user instruction. The volume slice region setting section 143 may be further configured to newly set a plurality of volume slice regions in response to the seventh user instruction. In one embodiment, if the seventh instruction for selecting a fourth 3-dimensional ultrasound image $3D_{324}$ among 3-dimensional ultrasound images $3D_{321}$-$3D_{327}$, which are shown in FIG. 8, is inputted, then the volume slice region setting section 143 may set the volume slice region corresponding to the fourth 3-dimensional ultrasound image $3D_{324}$ as a new reference volume slice region. Further, the volume slice region setting section 143 may set new second to fourth volume slice regions on the left of the new reference volume slice region, as well as new fifth to seventh volume slice regions on the right of the new reference volume slice region.

In another embodiment, if the seventh instruction for selecting a second 3-dimensional ultrasound image $3D_{322}$ among 3-dimensional ultrasound images $3D_{321}$-$3D_{327}$ is inputted, then the volume slice region setting section 143 may set the volume slice region corresponding to the second 3-dimensional ultrasound image $3D_{322}$ as a new reference volume slice region. Further, the volume slice region setting section 143 may set new second to fourth volume slice regions on the left of the new reference volume slice region, as well as new fifth to seventh volume slice regions on the right of the new reference volume slice region.

The processing unit 140 may further include a second image forming section 144. The second image forming section 144 may be configured to form 3-dimensional ultrasound images by using the ROIS and the volume slices.

The processing unit 140 may further include a layout setting section 145. The layout setting section 145 may set a layout having a plurality of display regions for displaying the plurality of 3-dimensional ultrasound image formed in the second image forming section 144 in response to the fourth user instruction. In one embodiment, if the fourth instruction for setting the layout is inputted, then the layout setting section 145 may set the layout having a size of 3×3, i.e., first to ninth display regions $DR_1$-$DR_9$, as illustrated in FIG. 7. Although the above embodiment has been described that the layout is set to have nine display regions, the layout may not be limited thereto. In one embodiment, the layout setting section 145 may set a layout to have twelve display regions (e.g., 4×3) or a layout to have twenty-four display regions (e.g., 6×4) in response to the fourth user instruction. Further, the layout setting section 145 may automatically set a layout to have predetermined numbers of display regions.

The processing unit 140 may further include an index setting section 146. The index setting section 146 may be configured to set indices at the respective display regions included in the layout. In one embodiment, the index setting section 146 may set a first index of "0" at a display region $DR_5$ for displaying a 3-dimensional ultrasound image $3D_{321}$ corresponding to the first volume slice set by the volume slice region 321 shown in FIG. 8. The index setting section 146 may set second and fourth indices of "−1" to "−3" at display regions $DR_3$, $DR_2$ and $DR_1$ for displaying 3-dimensional ultrasound images $3D_{322}$, $3D_{323}$ and $3D_{324}$ corresponding to the second to fourth volume slices set by the volume slice regions 322-324, respectively. Further, the index setting section 146 may set fifth to seventh indices of "+1" to "+3" at display regions $DR_7$, $DR_8$ and $DR_9$ corresponding to fifth to seventh volume slices set by the volume slice regions 325-327, respectively.

Although the above embodiment has been described that the indices are set at the display regions corresponding to the respective second to seventh volume slices set by the volume slice regions 322-327 with respect to the first volume slice region 321, the setting of the indices may not be limited thereto. In one embodiment, the index setting section 146 may set a first index of "0" at the display region $DR_3$ for displaying the 3-dimensional ultrasound image $3D_{322}$ corresponding to the second volume slice 322. In such a case, the index setting section 146 may set second to seventh indices of "1" to "6" at the display regions $DR_2$, $DR_1$, $DR_5$, $DR_7$, $DR_8$ and $DR_9$ corresponding to the volume slices set by the volume slice regions 323, 324, 321, 325, 326 and 327, respectively.

Although the above embodiments have been described that the indices are set by using the numerical values, the setting of the indices may not be limited thereto. In one embodiment, the indices may be set by different colors for the respective display regions.

The processing unit 140 may further include an OH forming section 147. The OH forming section 147 may be configured to form an OH view 410, which may 3-dimensionally indicate entire contours of the volume data and the reference plane therein, as illustrated in FIG. 8.

The processing unit 140 may further include an image processing section 148. The image processing section 148 may arrange the reference plane with the ROI set, the OH view 410 and the plurality of 3-dimensional ultrasound images $3D_{321}$-$3D_{327}$, the plurality of volume slices at the display regions included in the layout set in the layout setting section 145, as illustrated in FIG. 8. The image processing section 148 may further apply the indices to the respective display regions according to the indices set in the index setting section 146. The image processing section 148 may also control whether or not to indicate the reference plane and the OH view in the display regions in response to the fifth user instruction. The image processing section 148 may further form position information of the plurality of volume slice regions set on the reference plane image to thereby indicate the position information on the display region included in the layout.

Referring back to FIG. 1, the ultrasound system 100 may further include a display unit to display the layout containing the 3-dimensional ultrasound images, the reference plane image and the OH view. The ultrasound system 100 may further include a control unit 160. The control unit 160 may be configured to control the operations of entire elements included in the ultrasound system 100. In one embodiment, the control unit 160 may control the transmission and reception of the ultrasound signals. The control unit 160 may further control the formation and the display of the 3-dimensional ultrasound images.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
    an ultrasound probe including a plurality of transducer elements and configured to receive ultrasound echo signals reflected from a target object to acquire ultrasound data;
    a display configured to display a reference plane image based on a volume data formed by using the ultrasound data;
    a user input configured to receive a user instruction including a third user instruction for setting a plurality of volume slice regions respectively representing a plurality of rendering ranges of different widths in the volume data on the reference plane image to obtain a plurality of volume slices having the different widths; and
    a processor configured to perform a 3-dimensional ultrasound image rendering according to the plurality of rendering ranges of different widths to generate a plurality of 3-dimensional ultrasound images respectively corresponding to the plurality of volume slices having the different widths,
    wherein the display displays a screen including the plurality of 3-dimensional ultrasound images.

2. The ultrasound system of claim 1, wherein the processor forms is configured to form plane images corresponding to planes in the volume data,
    wherein the user input is configured to receive user instructions including:
    first user instructions for setting a region of interest (ROI) on each of the plane images;
    a second user instruction for selecting one of the planes as a reference plane;
    the third user instruction for setting the plurality volume slice regions for determining a plurality of rendering ranges of different widths on a reference plane image corresponding to the selected reference plane; and
    a fourth instruction for setting a layout including a plurality of display regions for displaying the plurality of 3-dimensional images.

3. The ultrasound system of claim 2, wherein the processor is further configured to:

form a plurality of plane images corresponding to the plurality of planes set in the volume data, wherein at least one of the planes is orthogonal to other planes in the volume data;

set the plurality of ROIs on the plurality of plane images in response to the first user instruction;

set the reference plane among the plurality of planes in response to the second user instruction and set the plurality of volume slice regions on the reference plane image to indicate rendering ranges of different widths in response to the third user instruction;

form the plurality of 3-dimensional ultrasound images corresponding to the plurality of volume slice regions by using the ROIs and the volume slices;

set the layout having the plurality of display regions for displaying the plurality of 3-dimensional ultrasound images in response to the fourth user instruction;

set indices to the respective display regions included in the layout according to the third and fourth user instructions; and arrange the plurality of 3-dimensional ultrasound images at the display regions included in the layout and set indices to the respective display regions according to the indices set in an index setting section.

4. The ultrasound system of claim 3, wherein the indices are numerical values or colors.

5. The ultrasound system of claim 3, wherein the processor is further configured to form an OH view 3-dimensionally indicating entire contours of the volume data and the reference plane set in the OH view.

6. The ultrasound system of claim 5, wherein the user input is configured to receive a fifth user instruction for determining whether or not to indicate the reference plane image and the OH view.

7. The ultrasound system of claim 6, wherein the processor is further configured to either indicate or not indicate the reference plane image and the OH view in response to the fifth user instruction.

8. The ultrasound system of claim 5, wherein the user instruction further includes a sixth user instruction for adjusting intervals between the plurality of volume slice regions.

9. The ultrasound system of claim 8, wherein the processor is further configured to adjust intervals between the plurality of volume slice regions in response to the sixth user instruction.

10. The ultrasound system of claim 5, wherein the processor is further configured to form position information of the plurality of volume slice regions set on the reference plane image to display the position information on at least one of the display regions included in the layout.

11. The ultrasound system of claim 5, wherein the user input is configured to receive a seventh user instruction for selecting a reference volume slice region from the plurality of volume slice regions.

12. The ultrasound system of claim 11, wherein the processor is further configured to set a plurality of new volume slice regions with respect to the reference volume slice region selected in response to the seventh user instruction.

13. The ultrasound system of claim 12, wherein the display is further configured to display the layout.

14. A method of providing a plurality of 3-dimensional ultrasound images, comprising:

a) receiving ultrasound echo signals reflected from a target object to acquire ultrasound data;

b) displaying a reference plane image based on a volume data formed by using the ultrasound data;

c) receiving, via a user input, a user instruction including a third user instruction for setting a plurality of volume slice regions respectively representing a plurality of rendering ranges of different widths in the volume data on the reference plane image to obtain a plurality of volume slices having different widths; and d) performing 3-dimensional ultrasound image rendering according to the plurality of rendering ranges of different widths to generate a plurality of 3-dimensional ultrasound images respectively corresponding to the plurality of volume slices having the different widths; and e) displaying a screen including the plurality of 3-dimensional ultrasound images.

15. The method of claim 14, further comprising forming plane images corresponding to planes in the volume data, wherein the user instruction includes:

first user instructions for a regions of interest (ROI) on each of the plane images;

a second user instruction for selecting one of the planes as a reference plane;

the third user instruction for setting the plurality volume slice regions for determining a plurality of rendering ranges of different widths on a reference plane image corresponding to the selected reference plane; and a fourth instruction for setting a layout including a plurality of display regions for displaying the plurality of 3-dimensional images.

16. The method of claim 15, wherein the step c) includes:

forming a plurality of plane images corresponding to the plurality of planes set in the volume data, wherein at least one of the planes is orthogonal to other planes in the volume data;

setting the plurality of ROIs on the plurality of plane images in response to the first user instruction;

setting the reference plane among the plurality of planes in response to the second user instruction and the plurality of volume slice regions on the reference plane image to indicate rendering ranges of different widths in response to the third user instruction;

forming the plurality of 3-dimensional ultrasound images corresponding to the plurality of volume slice regions by using the ROIs and the volume slices;

setting the layout having the plurality of display regions for displaying the plurality of 3-dimensional ultrasound images in response to the fourth user instruction;

setting indices to the respective display regions included in the layout according to the third and fourth user instructions; and arranging the plurality of 3-dimensional ultrasound images at the display regions included in the layout and setting indices to the respective display regions according to the indices set in an index setting section.

17. The method of claim 16, wherein the indices are numerical values or colors.

18. The method of claim 16, wherein the step c) includes forming an orientation help (OH) view 3-dimensionally indicating entire contours of the volume data and the reference plane set in the volume data.

19. The method of claim 18, further comprising receiving, via the user input, a fifth user instruction for determining whether or not to indicate the reference plane image and the OH view.

20. The method of claim 19, wherein the step c) includes indicating or not indicating the reference plane image and the OH view in response to the fifth user instruction.

21. The method of claim 15, wherein the user instruction further includes a fifth user instruction for adjusting intervals between the plurality of volume slice regions.

22. The method of claim 21, wherein the step c) includes adjusting intervals between the plurality of volume slice regions in response to the fifth user instruction.

23. The method of claim 15, further comprising receiving, via the user input, a fifth user instruction for selecting a reference volume slice region from the plurality of volume slice regions.

24. The method of claim 23, wherein the step c) includes setting a plurality of new volume slice regions with respect to the reference volume slice region selected in response to the seventh user instruction.

25. The method of claim 14, wherein the c) includes:
   forming position information of the plurality of volume slice regions set on the reference plane image; and
   displaying the position information on at least one of the display regions in the layout.

26. The method of claim 25, further comprising displaying the layout.

* * * * *